(12) United States Patent
Kang

(10) Patent No.: US 12,151,126 B2
(45) Date of Patent: Nov. 26, 2024

(54) HANDPIECE CAPABLE OF ADJUSTING DEPTH OF FOCUS OF HIGH-INTENSITY FOCUSED ULTRASOUND

(71) Applicant: SHENB Co., Ltd., Seoul (KR)

(72) Inventor: Sun Young Kang, Seoul (KR)

(73) Assignee: SHENB Co., Ltd., Seoul (KR)

( * ) Notice: Subject to any disclaimer, the term of this patent is extended or adjusted under 35 U.S.C. 154(b) by 0 days.

(21) Appl. No.: 18/511,441

(22) Filed: Nov. 16, 2023

(65) Prior Publication Data

US 2024/0165432 A1 May 23, 2024

(30) Foreign Application Priority Data

Nov. 18, 2022 (KR) .................... 10-2022-0155493

(51) Int. Cl.
*A61N 7/02* (2006.01)
*A61N 1/36* (2006.01)
*A61N 7/00* (2006.01)

(52) U.S. Cl.
CPC ........... *A61N 7/02* (2013.01); *A61N 1/36021* (2013.01); *A61N 1/36034* (2017.08); *A61N 2007/0091* (2013.01)

(58) Field of Classification Search
CPC .. A61N 7/02; A61N 1/36021; A61N 1/36034; A61N 2007/0091
See application file for complete search history.

(56) References Cited

U.S. PATENT DOCUMENTS

| 2012/0109232 | A1* | 5/2012 | Mohn | .............. G08B 5/22 |
| | | | | 607/3 |
| 2021/0268299 | A1* | 9/2021 | Casalino | .............. A61N 2/006 |
| 2022/0008112 | A1* | 1/2022 | Sverdlik | .............. A61B 18/0206 |
| 2023/0061594 | A1* | 3/2023 | Jin | .............. A61B 8/403 |

FOREIGN PATENT DOCUMENTS

| CN | 213912016 U | * | 8/2021 | |
| KR | 10-2012-0040909 A | | 4/2012 | |
| KR | 10-1534434 B1 | | 7/2015 | |
| KR | 10-2020-0000754 A | | 1/2020 | |
| KR | 10-2020-0006861 A | | 1/2020 | |
| KR | 20-2022-0000119 U | | 1/2022 | |
| KR | 10-2551704 B1 | | 7/2023 | |
| WO | WO-2020013504 A1 | * | 1/2020 | .............. A61N 7/02 |

OTHER PUBLICATIONS

Korean Office Action issued on Feb. 10, 2023, in counterpart Korean Patent Application No. 10-2022-0155493 (5 pages in English, 4 pages in Korean).
Korean Office Action issued on Jun. 20, 2023, in counterpart Korean Patent Application No. 10-2022-0155493 (1 page in English, 8 pages in Korean).
International search report issued on Feb. 20, 2024, in counterpart International Patent Application No. PCT/KR2023/018399 (3 pages).

\* cited by examiner

*Primary Examiner* — Baisakhi Roy
*Assistant Examiner* — Kaitlyn E Sebastian
(74) *Attorney, Agent, or Firm* — NSIP Law

(57) ABSTRACT

The present disclosure provides a handpiece capable of adjusting the depth of focus, including a case, a cartridge installed to be movable in a vertical direction inside the case and having a transducer that emits ultrasonic waves, and a vertical movement unit mounted inside the case and moving the transducer in a vertical direction by a magnetic force.

6 Claims, 6 Drawing Sheets

HANDPIECE CAPABLE OF ADJUSTING DEPTH OF FOCUS OF HIGH-INTENSITY FOCUSED ULTRASOUND

CROSS-REFERENCE TO RELATED APPLICATIONS

This application claims priority to Korean Patent Application No. 10-2022-0155493, filed on Nov. 18, 2022, the entire contents of which are incorporated herein by reference.

TECHNICAL FIELD

The present disclosure relates to a handpiece capable of focusing ultrasonic waves under the skin of a patient, and, more specifically, to a handpiece capable of adjusting the depth at which ultrasonic waves are focused.

BACKGROUND

High-intensity focused ultrasound energy refers to energy collected by focusing ultrasound waves on a specific point.

Treatment using such high-intensity focused ultrasound energy is based on a thermal effect in which heat is generated when ultrasound waves are focused on a certain point, causing the temperature to rise rapidly.

Heat generated by high-intensity focused ultrasound energy burns and removes specific subcutaneous tissue such as an intradermal tumor, or may cause degeneration and regeneration of subcutaneous tissue so as to be used for skin care or plastic surgery such as procedures to erase wrinkles.

A handpiece for generating high-intensity focused ultrasonic energy includes a case and a transducer that is built into a cartridge mounted inside the case and generates ultrasonic waves.

However, in the case of conventional handpieces, because a cartridge is fixed at a specific point inside a handpiece case, there is a problem in that it has to be replaced with a cartridge with a built-in transducer with a different focal length in order to adjust the depth at which ultrasonic waves are focused under the skin.

In order to solve this problem, Korean Patent Application Publication No. 10-2012-0040909 disclosed a handpiece having a three-dimensional movement mechanism installed inside the handpiece case and capable of moving a transducer in forward and backward, left and right, and up and down directions.

However, the three-dimensional movement mechanism uses three electric motors and three lead screws connected to each of the motors to control the position of a transducer. Because this method based on electric motors and lead screws requires a complex structure, the transducer moves slowly, causing problems in that ultrasonic waves are focused on unwanted points under the skin or the power supplied to the transducer has to be cut off when the transducer moves.

The handpiece disclosed in Korean Patent Publication No. 10-1534434 cools a transducer by a water-cooling method, but cooling by this water-cooling method has a problem in that the structure is complicated and management is difficult.

Meanwhile, treatment using high-intensity focused ultrasound energy causes an increase in the temperature of subcutaneous tissue, so a person being treated may feel pain. Recently, interest in handpieces capable of appropriately and effectively managing such pain has been increasing.

SUMMARY

The present disclosure has been made in an effort to address the above-described problems and provide a handpiece capable of adjusting the depth at which high-intensity focused ultrasound is focused, which can quickly move a transducer and appropriately relieve pain in the skin of a person being treated.

The handpiece capable of adjusting the depth of focus according to the present disclosure may include a case, a cartridge installed to be movable in a vertical direction inside the case and having a transducer that emits ultrasonic waves, and a vertical movement unit mounted inside the case and moving the transducer in a vertical direction by a magnetic force.

The vertical movement unit may include a magnet installed inside the case and a magnetic body to which the transducer is fixed and that moves the transducer in a vertical direction while the distance between the magnet and the magnetic body is adjusted by a magnetic force.

The vertical movement unit further may include an elastic unit for separating the magnet and the magnetic body from each other.

The magnet may be an electromagnet.

The handpiece capable of adjusting the depth of focus may further include a horizontal movement unit for moving the vertical movement unit in a horizontal direction.

The horizontal movement unit may include a movement block to which the vertical movement unit is fixed and a screw rotating to move the movement block in a horizontal direction.

The handpiece capable of adjusting the depth of focus may further include a skin cooling unit disposed around an opening in the lower part of the case to cool the skin of a person being treated and an electrical muscle stimulation (EMS) skin stimulation unit located adjacent to the skin cooling unit and providing electrical stimulation to the skin of the person being treated.

The handpiece capable of adjusting the depth at which high-intensity focused ultrasound is focused according to the present disclosure may quickly move a transducer, preventing ultrasonic waves from being focused on unwanted subcutaneous points and appropriately relieving pain in a patient's skin.

DETAILED DESCRIPTION

Figure 1:
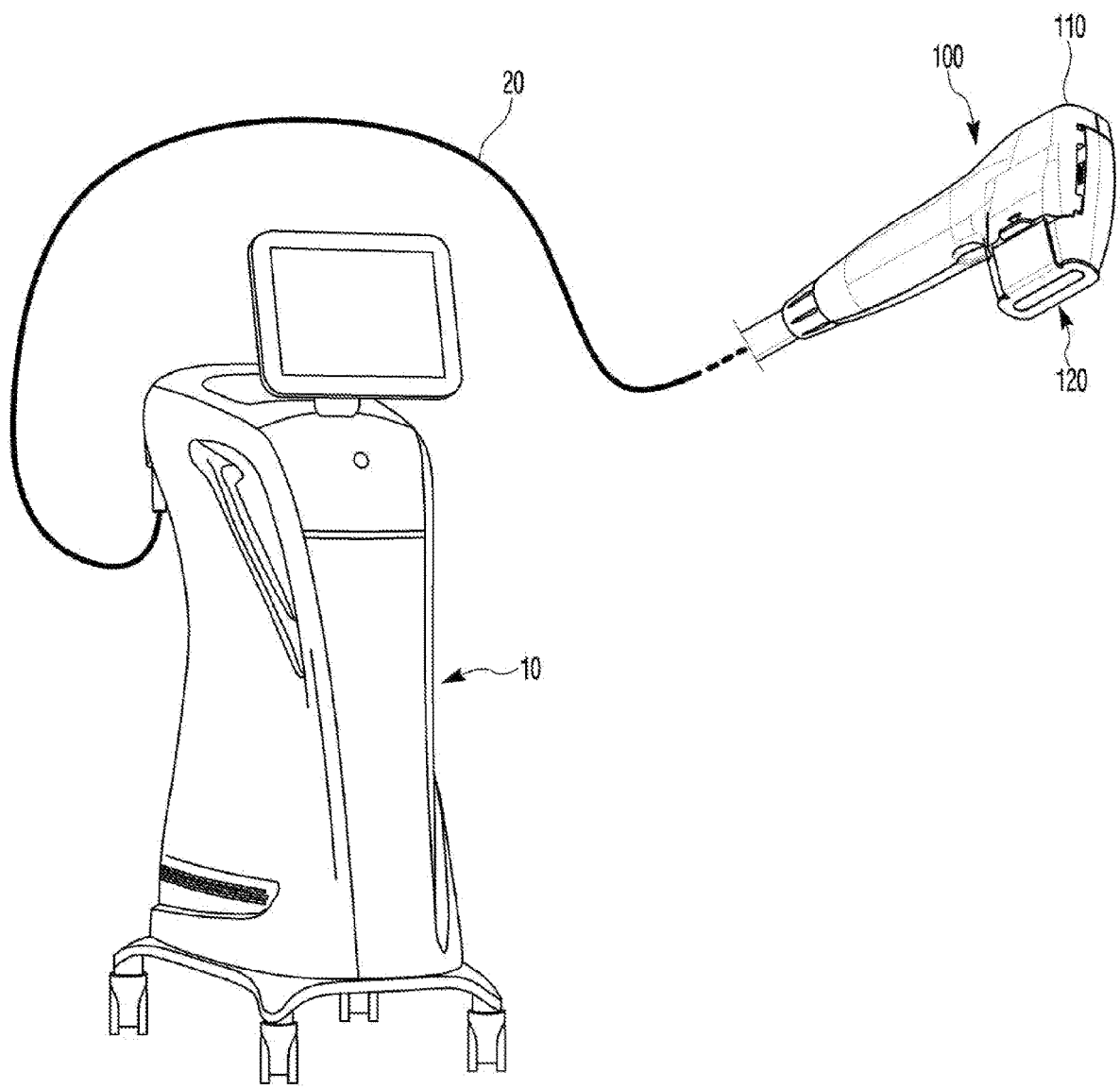
FIG. 1 is a perspective view of a handpiece capable of adjusting the depth at which high-intensity ultrasonic waves are focused and connected to a main controller according to an embodiment of the present disclosure.

Hereinafter, some embodiments of the present disclosure will be described in detail with reference to illustrative drawings. It should be noted that, when assigning reference numerals to components in each drawing, identical components have been given the same reference numerals as much as possible even when they are shown in different drawings.

In addition, in describing the embodiments of the present disclosure, when it is determined that detailed descriptions of related known features or functions impede understanding of the embodiments of the present disclosure, the detailed descriptions will not be provided.

Furthermore, to describe certain components in the embodiments of the present disclosure, terms such as first, second, A, B, (a), and (b) may be used. These terms are only used to distinguish the components from other components, and the nature, the sequence, the order, etc. of the components are not limited by the terms.

Figure 2:
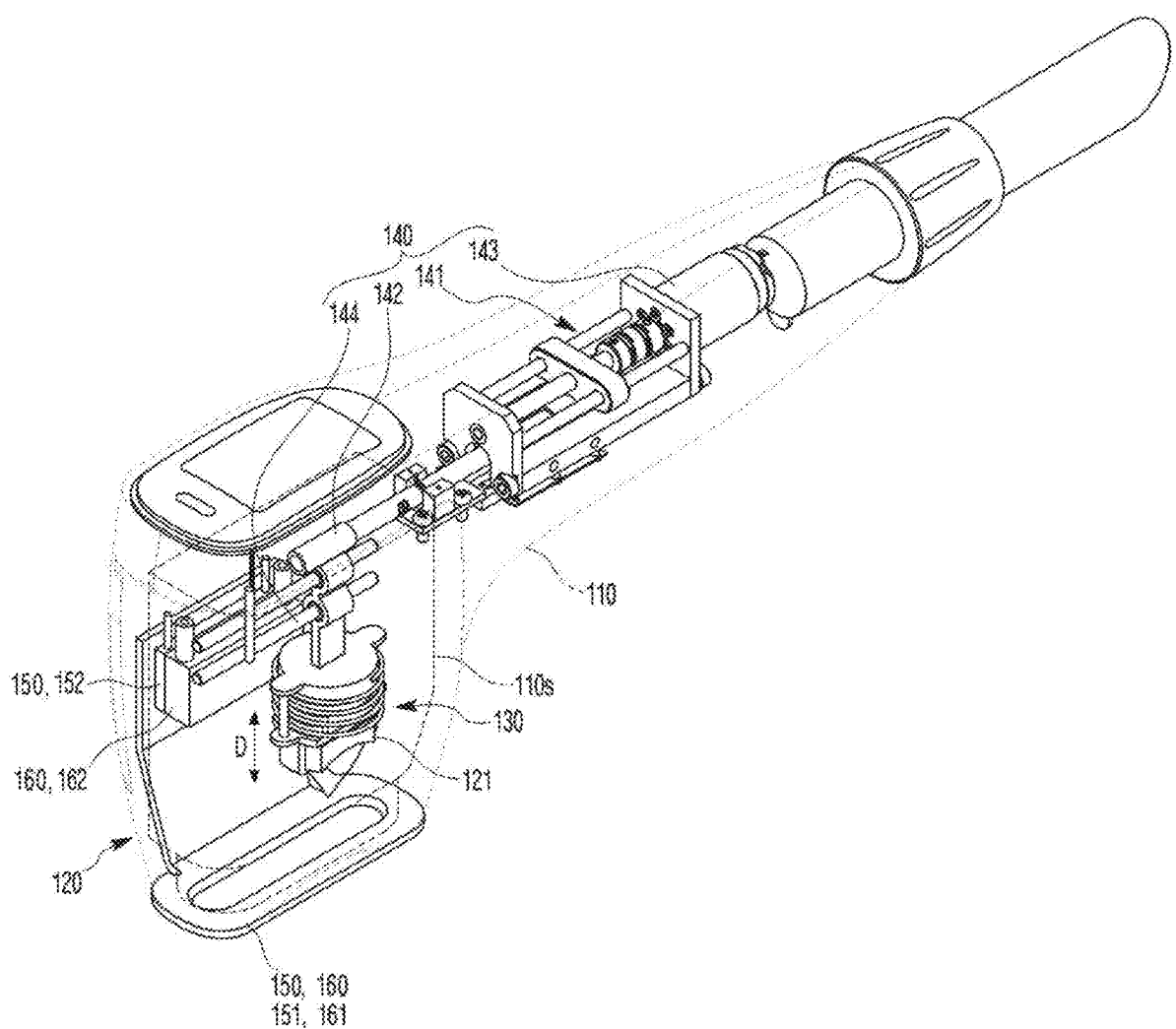
FIG. 2 is a view for illustrating components inside the handpiece in FIG. 1.
Figure 3:
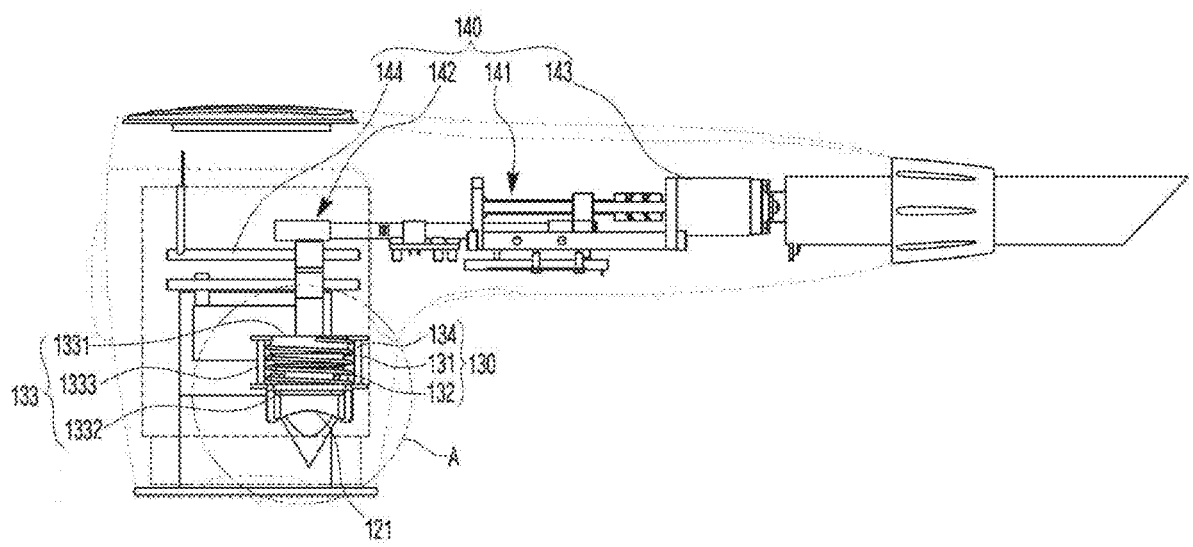
FIG. 3 is a front view of the handpiece in FIG. 2.
Figure 4:
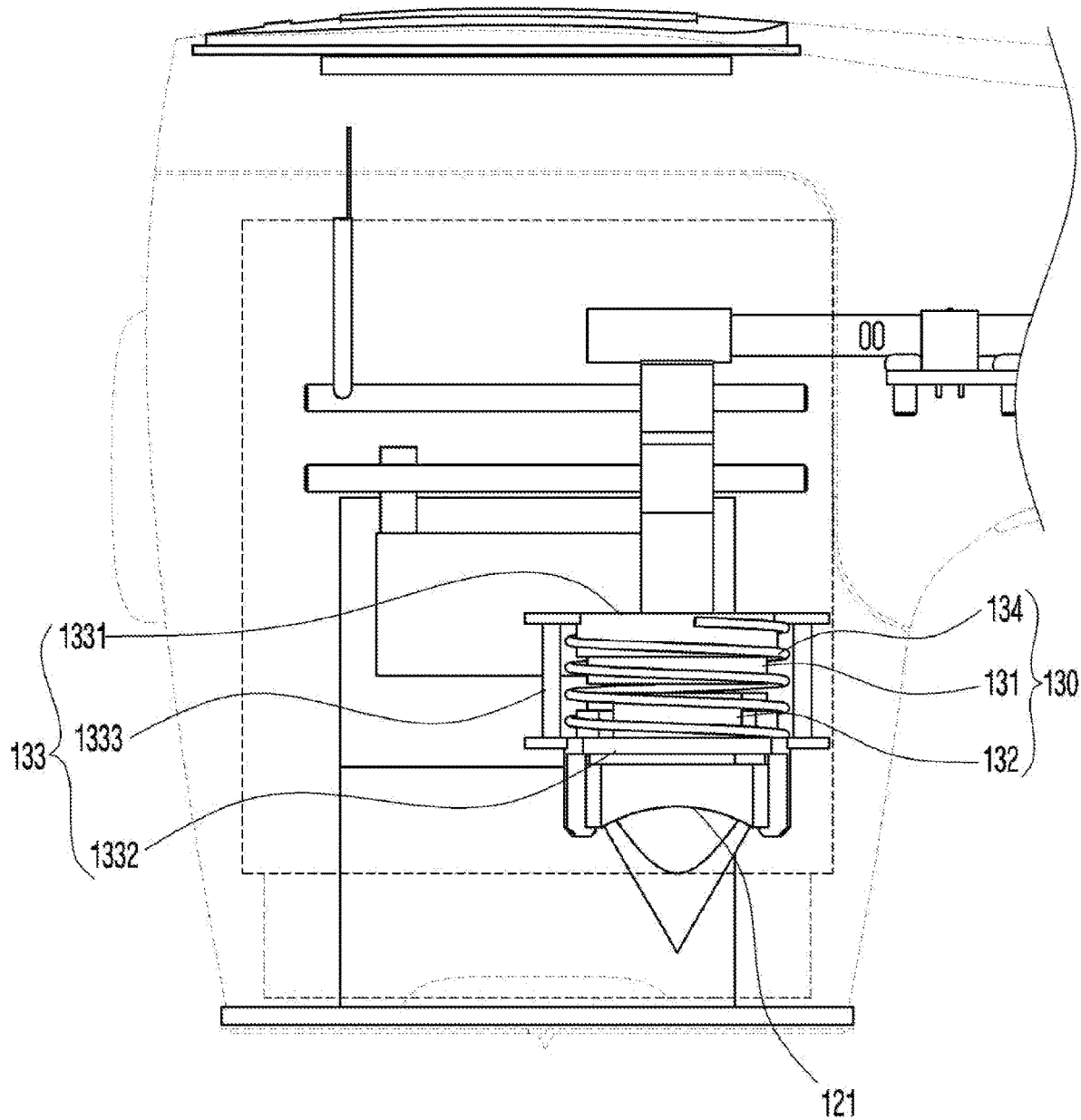
FIG. 4 is an enlarged view of part A in FIG. 3.
Figure 5:
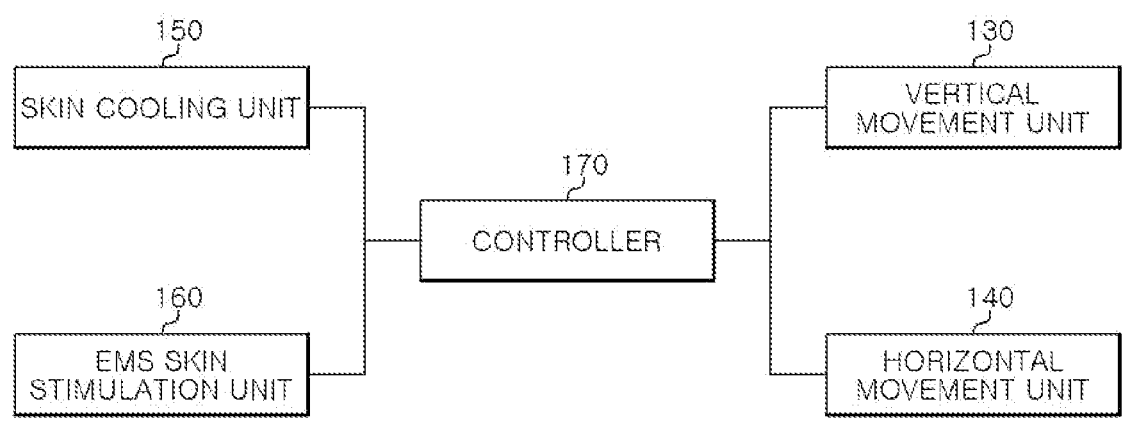
FIG. 5 is a partial block diagram of the handpiece in FIG. 2.
Figure 6:
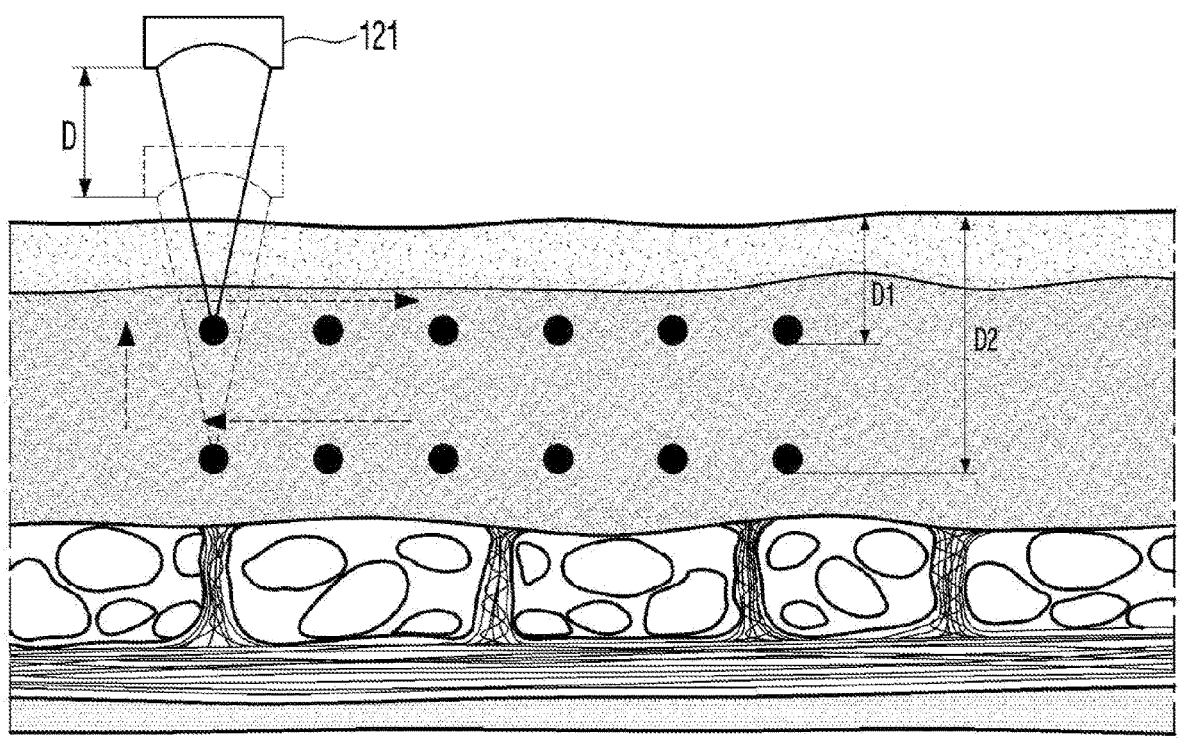
FIG. 6 is a view for illustrating how the handpiece in FIG. 2 operates.

FIG. 1 is a perspective view of a handpiece capable of adjusting the depth at which high-intensity ultrasonic waves are focused and connected to a main controller according to an embodiment of the present disclosure, FIG. 2 is a view for illustrating components inside the handpiece in FIG. 1, FIG. 3 is a front view of the handpiece in FIG. 2, FIG. 4 is an enlarged view of part A in FIG. 3, FIG. 5 is a partial block diagram of the handpiece in FIG. 2, and FIG. 6 is a view for describing how the handpiece in FIG. 2 operates.

Referring to FIGS. 1 to 5, a handpiece 100 capable of adjusting the depth of focus according to the present disclosure may be connected to a main controller 10 through a cable 20.

The main controller 10 may include a display, a CPU, a power unit, etc. and provide power and control signals to the handpiece 100 capable of adjusting the depth of focus.

The handpiece 100 capable of adjusting the depth of focus may be operated by the power, the control signals, etc. provided by the main controller 10.

Specifically, the handpiece 100 capable of adjusting the depth of focus may focus ultrasonic waves subcutaneously and generate heat to burn and remove specific subcutaneous tissue such as an intradermal tumor, or may cause degeneration and regeneration of subcutaneous tissue so as to be used for skin care or plastic surgery such as procedures to erase wrinkles.

The handpiece 100 capable of adjusting the depth of focus may include a case 110, a cartridge 120, and a vertical movement unit 130.

A mounting space 110s may be formed inside the case 110, the vertical movement unit 130 may be located inside the mounting space 110s, and the cartridge 120 may be mounted on the lower part of the case 110 and connected to the vertical movement unit 130.

An opening through which ultrasonic waves generated by a transducer 121 built into the cartridge 120 pass may be formed in the lower part of the case 110.

The vertical movement unit 130 may be mounted inside the case 110 and may move the transducer 121 in a vertical direction.

For example, the vertical movement unit 130 may move the transducer 121 in a vertical direction within a preset distance ranging from 1.5 mm to 4.5 mm, and may adjust the depth at which ultrasonic waves generated by the transducer 121 are focused.

However, a distance D at which the transducer 121 moves in a vertical direction by the vertical movement unit 130 according to the present disclosure is not limited to the above-mentioned distance.

The transducer 121 may be installed to move in vertical and horizontal directions inside the case 110 and may emit ultrasonic waves. In addition, the ultrasonic waves emitted by the transducer 121 may be focused under the skin of a patient, generating heat.

Since the vertical movement unit 130 may move the transducer 121 in a vertical direction according to the present disclosure, it may be possible for an operator to adjust the depth at which ultrasonic waves are focused under a patient's skin by moving the transducer 121 in a vertical direction with a simple operation without having to replace the cartridge 120 to adjust the focal distance of ultrasonic waves.

The vertical movement unit 130 may move the transducer 121 in a vertical direction with magnetic force.

Specifically, the vertical movement unit 130 may quickly adjust the depth at which ultrasonic waves are focused by immediately moving the transducer 121 in a vertical direction using magnetic force. Therefore, according to the present disclosure, it may be possible to minimize the focus of ultrasonic waves on subcutaneous points not requiring surgery.

The handpiece 100 capable of adjusting the depth of focus may further include a horizontal movement unit 140.

The horizontal movement unit 140 may be installed inside the case 110 and may move the vertical movement unit 130 in a horizontal direction.

The vertical movement unit 130 may include a magnet 131 and a magnetic body 132.

One of the magnet 131 and the magnetic body 132 may be installed inside the case 110, and the other may be installed in the transducer 121.

The magnetic body 132 may be located below or above the magnet 131 and may approach the magnet 131 by using the magnet 131 and magnetic force.

It may be desirable that the magnetic body 132 is a ferromagnetic body made of iron, cobalt, nickel, or an alloy thereof, but any material that can approach the magnet 131 by the magnetic force of the magnet 131 may be possible.

When the magnet 131 and the magnetic body 132 approach or move away from each other in a vertical direction in the space inside the case 110, the cartridge 120 may also move in a vertical direction.

Either the magnet 131 or the magnetic body 132 may be connected to the horizontal movement unit 140.

Hereinafter, for convenience of explanation, an example of the magnet 131 connected to the horizontal movement unit 140 will be described.

The magnetic body 132 may be installed to be guided by a guider 133 connected to the magnet 131 to be movable in a vertical direction.

The guider 133 may include a first holder 1331, a second holder 1332, and a guide pin 1333.

The upper side of the first holder 1331 may be connected to the horizontal movement unit 140, and the magnet 131 may be fixed to the lower side of the first holder 1331.

In addition, the guide pin 1333 may be formed to extend downward at the edge of the first holder 1331.

The magnetic body 132 may be fixed to the upper surface of the second holder 1332, and the transducer 121 may be fixed to the lower surface of the second holder 1332.

The second holder 1332 may be guided to move in a vertical direction by the guide pin 1333.

Specifically, a plurality of guide holes through which the plurality of guide pins 1333 each pass may be formed on the second holder 1332. Therefore, the vertical movement of the second holder 1332 may be guided by the guide pin 1333 inserted into the guide hole of the second holder 1332.

The magnet 131 may be an electromagnet.

As current is applied to the magnet 131, an attractive force may act between the magnet 131 and the magnetic body 132, closing the distance between the magnet 131 and the magnetic body 132.

Meanwhile, the vertical movement unit 130 may further include an elastic unit 134.

The elastic unit 134 may be an elastic body that can separate the magnet 131 and the magnetic body 132 from each other.

When the elastic unit 134 separates the magnet 131 and the magnetic body 132 from each other, as a current is applied to the magnet 131, the amount of the attractive force between the magnet 131 and the magnetic body 132 may be adjusted based on the intensity of the applied current, thereby adjusting the distance between the magnet 131 and the magnetic body 132.

For example, the elastic unit 134 may widen the distance between the magnet 131 and the magnetic body 132 by elastic restoring force when the intensity of the current applied to the magnet 131 is below a set level.

In addition, when the intensity of the current applied to the magnet 131 is above a set level, the attractive force between the magnet 131 and the magnetic body 132 may close the distance between the magnet 131 and the magnetic body 132.

The horizontal movement unit 140 may include a screw 141, a movement block 142, and a motor 143.

The screw 141 may be installed in a horizontal direction inside the case 110 and may rotate by the motor 143.

The movement block 142 may move forward and backward in a horizontal direction depending on the direction in which the screw 141 is rotating.

The movement block 142 may be connected to the first holder 1331 of the vertical movement unit 130 so as to move the vertical movement unit 130 in a horizontal direction.

Therefore, the transducer 121 may move in a horizontal direction. The transducer 121 may emit ultrasonic waves while moving forward or backward in a horizontal direction.

In addition, when the cartridge 120 moves forward or backward in a horizontal direction, the vertical movement unit 130 may adjust the position of the cartridge 120 in a vertical direction.

For example, when the transducer 121 moves forward by the horizontal movement unit 140, the ultrasonic waves emitted from the transducer 121 may be focused to a second depth of focus D2, and, when the transducer 121 moves backward by the horizontal movement unit 140, the transducer 121 may be moved upward by a preset distance D by the vertical movement unit 130 and then emit ultrasonic waves to a first depth of focus D1 (see FIG. 6).

According to the present disclosure, the method of moving the transducer 121 by the horizontal movement unit 140 and the vertical movement unit 130 is not limited to the above-described method, and can be modified in various ways.

The horizontal movement unit 140 may further include a guide bar 144.

The guide bar 144 may guide the horizontal movement of the movement block 142.

The handpiece 100 capable of adjusting the depth of focus may further include a skin cooling unit 150.

The skin cooling unit 150 may be disposed around the opening in the lower part of the case 110.

The skin cooling unit 150 may be exposed to the outside of the case 110, and may be in contact with the skin of a person being treated during the procedure and quickly absorb heat from the skin of the person, thereby reducing pain in the skin of the person.

Specifically, when the cartridge 120 emits ultrasonic waves, the skin cooling unit 150 may come into contact with the skin of a person being treated and quickly absorb heat from the skin of the person.

The handpiece 100 capable of adjusting the depth of focus may further include an electrical muscle stimulation (EMS) skin stimulation unit 160.

The EMS skin stimulation unit 160 may stimulate the skin of a person being treated by flowing a micro-current to the skin of the person, thereby reducing pain in the skin of the person.

Cooling of a patient's skin by the skin cooling unit 150 and stimulating of the patient's skin by the EMS skin stimulation unit 160 may proceed independently or simultaneously.

The skin cooling unit 150 may include a cooling plate 151 and a thermoelectric element 152.

The cooling plate 151 may be disposed around the opening in the lower part of the case 110 and come into contact with the skin of a person being treated.

The thermoelectric element 152 may be in contact with the cooling plate 151 to absorb heat from the cooling plate 151 and cool the cooling plate 151.

For example, the thermoelectric element 152 may include a Peltier module made of $Bi_2TeO_3$, and may convert heat energy absorbed from the cooling plate 151 into electrical energy.

The thermoelectric element 152 may cool the cooling plate 151 to a temperature of 0° C. to 15° C. The cooling plate 151 may absorb heat from the skin heated by the ultrasonic waves that have been emitted from the transducer 121 and then focused, thereby easing pain in the skin of a person being treated.

The EMS skin stimulation unit 160 may include an EMS pad 161 and an EMS control module 162.

The EMS control module 162 may control the current transmitted from the EMS pad 161 to the skin. Accordingly, the EMS pad 161 may provide electrical stimulation for relieving pain to the skin of a person being treated.

The cooling plate 151 and the EMS pad 161 may be formed integrally, or the EMS pad 161 may be attached to a predetermined portion of the cooling plate 151.

The EMS control module 162 may control the EMS pad 161 to apply a microcurrent with an intensity of 1 mA to 100 mA and a frequency of 0 kHz to 10 kHz to the skin of a person being treated.

The handpiece 100 capable of adjusting the depth of focus may further include a controller 170.

The controller 170 may be connected to each of the vertical movement unit 130, the horizontal movement unit 140, and the skin cooling unit 150.

The controller 170 may control driving of the horizontal movement unit 140 and the vertical movement unit 130 and the operation of the skin cooling unit 150.

Example 1_Control of Skin Cooling Temperature and Skin Irritation

While a patient is receiving a treatment using focused ultrasonic waves, the temperature of the cooling plate 151 may be controlled to 3° C. to 5° C., and the intensity and the frequency of the microcurrent of the EMS pad 161 may be controlled to 80 mA to 100 mA and 1 kHz to 10 kHz, respectively.

Comparative Example 1_Skin Cooling Temperature

While a patient is receiving a treatment using focused ultrasonic waves, the temperature of the cooling plate 151 may be controlled to 3° C. to 5° C., and the intensity of the microcurrent of the EMS pad 161 may be controlled to 0 mA.

Experimental Example 1_Experiment on Patient's Pain

Twenty female patients in their 40 s weighing between 48 kg and 73 kg were the subjects of the experiment, and the subjects were randomly divided into Group A and Group B, each having 10 subjects. In the case of Group A, an increase or decrease in pain was observed while a treatment using focused ultrasonic waves was performed on wrinkles around the right eye of the patients under the conditions of Comparative Example 1 after a treatment using focused ultrasonic waves had been performed on wrinkles around the left eye of the patients under the conditions of Example 1. In the case of Group B, an increase or decrease in pain was observed while a treatment using focused ultrasonic waves was performed on wrinkles around the right eye of the patients under the conditions of Example 1 after a treatment using focused ultrasonic waves had been performed on wrinkles around the left eye of the patients under the conditions of Comparative Example 1.

When the treatment under the conditions of Comparative Example 1 began after the treatment under the conditions of Example 1, all the subjects in Group A felt an increase in pain, and Table 1 below shows how much pain increased in the subjects in Group A.

In Table 1 below, a score of 5 was given when subjects felt a significant increase in pain, 4 was given when subjects felt a significant increase in pain, 3 was given when subjects felt a moderate increase in pain, 2 was given when subjects felt a slight increase in pain, and 1 was given when subjects did not feel an increase in pain.

TABLE 1

| Subject | 1 | 2 | 3 | 4 | 5 | 6 | 7 | 8 | 9 | 10 |
|---|---|---|---|---|---|---|---|---|---|---|
| Increase in Pain | 4 | 4 | 4 | 5 | 5 | 4 | 4 | 3 | 5 | 5 |

All the subjects in Group A experienced a significant increase in pain when the treatment under the conditions of Comparative Example 1 began after the treatment under the conditions of Example 1.

All the subjects in Group B felt pain relief when the treatment under the conditions of Example 1 began after the treatment under the conditions of Comparative Example 1. Table 2 below shows how much pain relief the subjects in Group B felt.

In Table 2 below, a score of A was given when subjects felt very great pain relief, B was given when subjects felt great pain relief, C when was given subjects felt moderate pain relief, D was given when subjects felt slight pain relief, and F was given when subjects did not feel pain relief.

TABLE 2

| Subject | 1 | 2 | 3 | 4 | 5 | 6 | 7 | 8 | 9 | 10 |
|---|---|---|---|---|---|---|---|---|---|---|
| Decrease in Pain | A | A | A | B | A | A | B | A | C | A |

All the subjects in Group B experienced significant pain relief when the treatment under the conditions of Example 1 began after the treatment under the conditions of Comparative Example 1. In other words, it was confirmed that pain in the skin of a person receiving the treatment was greatly alleviated when the treatment using focused ultrasonic waves was performed according to Example 1 of the present disclosure.

All components in the embodiments of the present disclosure have been described as being combined or operating in combination, but the present disclosure is not necessarily limited to the embodiments. That is, one or more of the components may be selectively combined to operate within the scope of the purpose of the present disclosure.

In addition, unless defined otherwise, all terms used herein, including technical or scientific terms, have a meaning consistent with the meaning commonly understood by a person having ordinary skills in the technical field to which the present disclosure belongs. Commonly used terms such as terms defined in dictionaries should be interpreted as having meanings consistent with the meanings in the context of the related technology, and should not be construed in an ideal or overly formal sense unless explicitly defined in the present disclosure.

The description above is only an exemplary description of the technology of the present disclosure, and various modifications and changes within the scope of the essential characteristics of the present disclosure will be possible to a person having ordinary skill in the technical field to which the present disclosure belongs. Therefore, the embodiments disclosed in the present disclosure are not intended to limit the technology of the present disclosure, but to explain them, and the scope of the technology of the present disclosure is not limited by the embodiments. The scope of the present disclosure should be determined based on the following claims, and all technologies within the scope equivalent thereto should be deemed to be included in the scope of the present disclosure.

The invention claimed is:

1. A handpiece capable of adjusting the depth of focus, comprising:
    a case;
    a cartridge installed to be movable in a vertical direction inside the case and having a transducer that emits ultrasonic waves;
    a vertical mover mounted inside the case and moving the transducer in a vertical direction by a magnetic force;
    a skin cooler disposed around an opening in the lower part of the case to cool the skin of a person being treated; and
    an electrical muscle stimulation (EMS) skin stimulator located adjacent to the skin cooler and providing electrical stimulation to the skin of the person being treated,
    wherein the skin cooler includes: a cooling plate disposed around the opening in the lower part of the case and in contact with the skin of the person; and a thermoelectric element that is in contact with the cooling plate and absorbs heat from the cooling plate to cool the cooling plate,
    the EMS skin stimulator includes: an EMS pad that is formed unitarily with the cooling plate or is located in a center or an edge of the cooling plate and provides electrical stimulation for relieving pain to the skin of the person; and an EMS control module for controlling the EMS pad,
    the temperature of the cooling plate is controlled to 3° C. to 5° C., and the electrical stimulation of the EMS pad is a current with an intensity of 80 mA to 100 mA and a frequency of 1 kHz to 10 KHz.

2. The handpiece capable of adjusting the depth of focus of claim 1, wherein the vertical mover includes: a magnet installed inside the case; and a magnetic body to which the transducer is fixed and that moves the transducer in a vertical direction while the distance between the magnet and the magnetic body is adjusted by a magnetic force.

3. The handpiece capable of adjusting the depth of focus of claim 2, wherein the vertical mover further includes an elastic structure for separating the magnet and the magnetic body from each other.

4. The handpiece capable of adjusting the depth of focus of claim 2, wherein the magnet is an electromagnet.

5. The handpiece capable of adjusting the depth of focus of claim 1, further comprising a horizontal mover for moving the vertical mover in a horizontal direction.

6. The handpiece capable of adjusting the depth of focus of claim 5, wherein the horizontal mover includes a movement block to which the vertical mover is fixed and a screw rotating to move the movement block in a horizontal direction.

\* \* \* \* \*